(12) United States Patent
Lamura et al.

(10) Patent No.: US 9,840,733 B2
(45) Date of Patent: **\*Dec. 12, 2017**

(54) APPARATUS FOR USE IN ISOTHERMAL AMPLIFICATION

(71) Applicant: DNAE GROUP HOLDINGS LIMITED, London (GB)

(72) Inventors: Maurizio Lamura, London (GB); Angel Chan-Ju Wang, London (GB); Alpesh Patel, London (GB)

(73) Assignee: DNAE GROUP HOLDINGS LIMITED, London (GB)

( \* ) Notice: Subject to any disclaimer, the term of this patent is extended or adjusted under 35 U.S.C. 154(b) by 0 days.

This patent is subject to a terminal disclaimer.

(21) Appl. No.: 15/282,879

(22) Filed: Sep. 30, 2016

(65) Prior Publication Data

US 2017/0016058 A1    Jan. 19, 2017

Related U.S. Application Data

(63) Continuation of application No. 14/232,817, filed as application No. PCT/GB2012/051694 on Jul. 16, 2012, now Pat. No. 9,469,870.

(30) Foreign Application Priority Data

Jul. 14, 2011    (GB) .................................. 1112140.7

(51) Int. Cl.
C12P 19/34      (2006.01)
C12Q 1/68       (2006.01)
G01N 27/414     (2006.01)

(52) U.S. Cl.
CPC ......... *C12Q 1/6858* (2013.01); *C12Q 1/6825* (2013.01); *C12Q 1/6844* (2013.01); *C12Q 1/6848* (2013.01); *G01N 27/414* (2013.01)

(58) Field of Classification Search
USPC .............................................. 435/6.12, 91.2
See application file for complete search history.

(56) References Cited

U.S. PATENT DOCUMENTS

| | | |
|---|---|---|
| 7,686,929 B2 | 3/2010 | Toumazou et al. |
| 7,888,015 B2 | 2/2011 | Toumazou et al. |
| 8,114,591 B2 | 2/2012 | Toumazou et al. |
| 9,469,870 B2 | 10/2016 | Lamura et al. |
| 2004/0134798 A1 | 7/2004 | Toumazou et al. |
| 2005/0089898 A1 | 4/2005 | Boyd et al. |
| 2005/0282202 A1 | 12/2005 | Brolaski et al. |
| 2008/0032295 A1 | 7/2008 | Toumazou et al. |
| 2009/0111159 A1 | 4/2009 | Brolaski et al. |
| 2010/0056410 A1 | 3/2010 | Visintin et al. |
| 2010/0087641 A1 | 4/2010 | Boyd et al. |
| 2010/0151479 A1 | 6/2010 | Toumazou et al. |
| 2010/0255595 A1 | 10/2010 | Toumazou et al. |
| 2011/0217697 A1 | 9/2011 | Rothberg et al. |
| 2012/0021918 A1 | 1/2012 | Bashir |
| 2012/0042898 A1 | 2/2012 | Visintin et al. |
| 2012/0175252 A1 | 7/2012 | Toumazou et al. |

FOREIGN PATENT DOCUMENTS

| | | |
|---|---|---|
| WO | 03/073088 | 9/2003 |
| WO | 2005/021802 | 3/2005 |
| WO | 2008/039730 | 4/2008 |
| WO | 2008/107014 | 9/2008 |
| WO | 2009/071664 | 6/2009 |
| WO | 2010/008480 | 1/2010 |

OTHER PUBLICATIONS

Hanaki et al. "Loop-mediated isothermal amplification assays for identification of antiseptic-and methicillin-resistant *Staphylococcus aureus*" Journal of Microbiological Methods, vol. 84, No. 2, pp. 251-254 (Feb. 2001).
Liang et al. "Development of loop-mediated isothermal amplification assay for detection of *Entamoeba histolytica*" Journal of Clinical Microbiology, vol. 47, No. 6, pp. 1892-1895 (Jun. 2009).
Notomi et al. "Loop-mediated isothermal amplication of DNA" Nucleic Acids Research, vol. 28, No. 12, E63, seven pages (Jun. 2000).
Purushothaman et al. "Protons and single nucleotife polymorphism detection: A simple use for the Ion Sensitive Field Effect Transistor" Sensors and Actuators B: Chemical, vol. 114, No. 2, pp. 964-968 (Apr. 2006).
Sakurai & Husimi "Real-time monitoring of DNA polymerase reactions by a micro ISFET pH sensor" Analytical Chemistry, vol. 64, No. 17, pp. 1996-1997 (Sep. 1992).
Soejima et al. "Rapid detection of haptoglobin gene deletion in alkaline-denatured blood by loop-mediated isothermal amplication reaction" Journal of Molecular Diagnostics, vol. 13, No. 3, pp. 334-339 (May 2011).
Int'l Search Report for PCT/IB2012/051694, four pages, dated Sep. 10, 2012.
Written Opinion for PCT/IB2012/051694, seven pages, dated Sep. 10, 2012.
Int'l Preliminary Report on Patentability for PCT/IB2012/051694, eight pages, dated Jan. 14, 2014.

*Primary Examiner* — Kenneth Horlick
(74) *Attorney, Agent, or Firm* — Nixon & Vanderhye PC

(57) ABSTRACT

An apparatus for monitoring amplification of a nucleic acid by providing a pH sensor or pH indicator, a nucleic acid in an amplification mixture, and an isothermal amplification enzyme.

20 Claims, 7 Drawing Sheets

APPARATUS FOR USE IN ISOTHERMAL AMPLIFICATION

This application is a continuation of application Ser. No. 14/232,817, filed 14 Jan. 2014, now Pat. No. 9,469,870; which is the U.S. national phase of Application No. PCT/GB2012/051694, filed 16 Jul. 2012, which claims priority to application Ser. No. GB 1112140.7, filed 14 Jul. 2011; the entire contents of each of which are hereby incorporated by reference.

FIELD OF THE INVENTION

The present invention relates to a method and kit for amplifying a quantity of nucleic acid. The invention is particularly relevant to isothermal amplification techniques. The amplified nucleic acid may be detected by a sensor.

BACKGROUND

When performing genetic analysis, there is generally a need to amplify the number of copies in the sample, as the number present in the sample is generally too few to be detected.

This can be done using, for example, thermocycling or isothermal amplification.

Isothermal techniques include SDA, LAMP, SMAP, ICAN, SMART. The reaction proceeds at a constant temperature using strand displacement reactions. Amplification can be completed in a single step, by incubating the mixture of samples, primers, DNA polymerase with strand displacement activity, and substrates at a constant temperature. In one technique, called Loop-mediated isothermal amplification (LAMP), target-specific amplification is achieved by the use of 4 to 6 different primers specifically designed to recognize 6 to 8 distinct regions on the target gene, respectively. LAMP is further described in Eiken Chemical's patent EP2045337 'Process for synthesizing nucleic acid', incorporated here by reference.

Such methods typically amplify nucleic acid copies $10^9$-$10^{10}$ times in 15-60 minutes.

In addition to the primers, strand displacement techniques use Tris and sulphate compounds (such as MgSO4, NH4SO4) to maintain enzyme functionality.

Tris is an organic compound (more formally known as tris (hydroxymethyl) aminomethane, with the formula (HOCH2)3CNH2). Strand displacement techniques, such as LAMP, use Tris as a buffer, which maintain the reaction at the optimal pH.

The recommended concentration of Tris and Sulphates is 20 mM or more and 12-20 mM respectively.

Once the nucleic acid is amplified, a nucleic acid assay requires a secondary detection technology such as spectrophotometry, turbidity, LFD (lateral flow dipsticks) or luciferase. However, such known techniques have drawbacks. Fluorescent reagents require labelling to allow UV fluorescence, making it expensive. Furthermore, reagents such as SYBR green binds to DNA making it inherently carcinogenic; the Ames Test shows it to be both mutagenic and cytotoxic. Also SYBR green is not specific and attaches to any double stranded DNA thus increasing background signal. Turbidity measurements require expensive instrumentation to provide quantification. Lastly, the reagents used in LFD require secondary conjugation which is susceptible to non-specific detection.

The existing isothermal techniques are not suitable for systems employing pH detection. Thus there is a need in the art for a kit and method for isothermally amplifying nucleic acids and efficiently detecting them with a safe inexpensive device. Surprisingly, the inventors have found that the reagents used may increase the yield of amplification.

SUMMARY OF THE INVENTION

According to a first aspect of the invention there is provided a kit of reagents combinable to form a mixture for use in isothermally amplifying a nucleic acid, the kit of reagents comprising: a magnesium salt, a quaternary ammonium salt, an alkali base.

The buffer capacity of the mixture may be set to less than an expected concentration of protons released during amplification divided by a threshold pH change to be detected by a sensor exposed to the mixture.

The buffer capacity of the mixture may be set to less than one half of an expected concentration of protons released during amplification divided by a threshold pH change to be detected by a sensor exposed to the mixture.

The threshold pH change to be detected may be the limit of detection of said sensor.

The buffer capacity of the mixture at the operating conditions for the amplification may be less than 10 mM, preferably less than 5 mM, more preferably less than 1 mM.

The concentration of buffering agents in the mixture may be less than 5 mM, more preferably less than 3 mM, less than 2 mM, or less than 1 mM.

The concentration of sulphate compounds, if present, may be less than 15 mM, preferably less than 10 mM, less than 8 mM, less than 5 mM, or less than 1 mM.

The concentration of the quaternary ammonium salt, preferably ammonium chloride, is between 2 mM and 15 mM.

The concentration of the alkali base sets the pH of the mixture between 6 and 9, preferably between 7 and 8.8, more preferably between 8.3 and 8.6.

The alkali base is one of NaOH, KOH or LiOH.

There may also be one or more primers used in the amplification of the nucleic acid, which primers are allele specific such that amplification indicates the presence of a target nucleic acid.

The isothermal amplification may be Strand Displacement amplification, preferably Loop-mediated isothermal amplification (LAMP).

The buffering capacity of the mixture may substantially mask the expected amount of protons released in the absence of amplification.

There kit may also have a strand displacement enzyme, nucleotides, and primers, preferably wherein at least one of these is stored separately from the remaining reagents. According to a second aspect of the invention there is provided a method of using a kit of reagents for isothermal amplification a pH sensor or pH indicator, amplifying the nucleic acid using isothermal amplification; and detecting a change in pH due to the amplification using the pH sensor or pH indicator.

The pH indicator may be a colorimetric or fluorescent dye and the pH sensor may be an Ion Sensitive Field Effect Transistor (ISFET).

The method may determine a reaction time needed to change the pH of the mixture greater than a predetermined amount of change and quantifying a starting concentration of the nucleic acid based on the reaction time.

The mixture may be in fluid communication with a reference electrode, preferably a Silver-Silver Chloride electrode.

The mixture may comprise one or more allele specific primers having at least one base complementary to a target Single Nucleotide Polymorphism (SNP) of the nucleic acid, the method further comprising identifying said at least one base of the nucleic acid depending on whether amplification proceeds, as detected by the pH sensor or pH indicator.

The amplification may change the proton concentration of the mixture by more than 10% of the buffer capacity of the mixture.

According to a third aspect of the invention there is provided a method comprising isothermally amplifying a nucleic acid using the novel kit of reagents.

BRIEF DESCRIPTION OF THE DRAWINGS

Specific embodiments of the invention will now be described by way of example only with reference to the accompanying figures, in which.

Conventional LAMP amplification methods use DNA polymerases with displacement activity under standard assay conditions such as: 20 mM Tris-HCl (pH8.8), 10 mM KCl, 10 mM (NH)4SO4, 2.5 mM MgSO4. 0.1% Triton X-100, 0.8M Betaine, DNA/RNA, dNTP and Bst polymerase.

The inventors found that these conventional reagents do not permit detection by pH sensors primarily because of their ability to mask the production of protons during amplification.

Indeed, all these constituents have a different pKa which means they have a different impact on the buffer capacity of the mixture.

Among the above mentioned reagents, TrisHCl has the ability to absorb counter ions (H+ and OH−) so as to help keep the solution at a stable pH level within a range optimal for the polymerase to act.

The inventors found that replacing TrisHCl with NaOH reduces the buffer capacity while setting the pH to where polymerase (such as Bst) can operate. Moreover, NaOH makes the two strands in double-stranded DNA less stringently bound, allowing displacement polymerase to break them apart more easily, thus speeding up the reaction and increase the efficiency of the strand displacement enzyme.

Additionally, electronic sensors, such as ISFETs, use reference electrodes such as Platinum, Ag/AgCl, calomel, etc. Some of these materials, in particular Ag/AgCl electrodes, react with these standard reagents. For instance, with Ag/AgCl electrodes Tris forms a Tris-Ag complex on the electrode which deteriorates the Ag/AgCl performance and Sulphate-containing reagents can poison the Ag/AgCl electrode.

DETAILED DESCRIPTION

A preferred system using the present method comprises a pH sensor or indicator, microfluidic structure, a, nucleic acid sample, reagents, and a reference electrode when needed to set a voltage potential of the sample. The reagents and sample are combined into one fluid to enable amplification. Protons are released during amplification and the change in pH is measured with a pH sensor or indicator.

Figure 3:
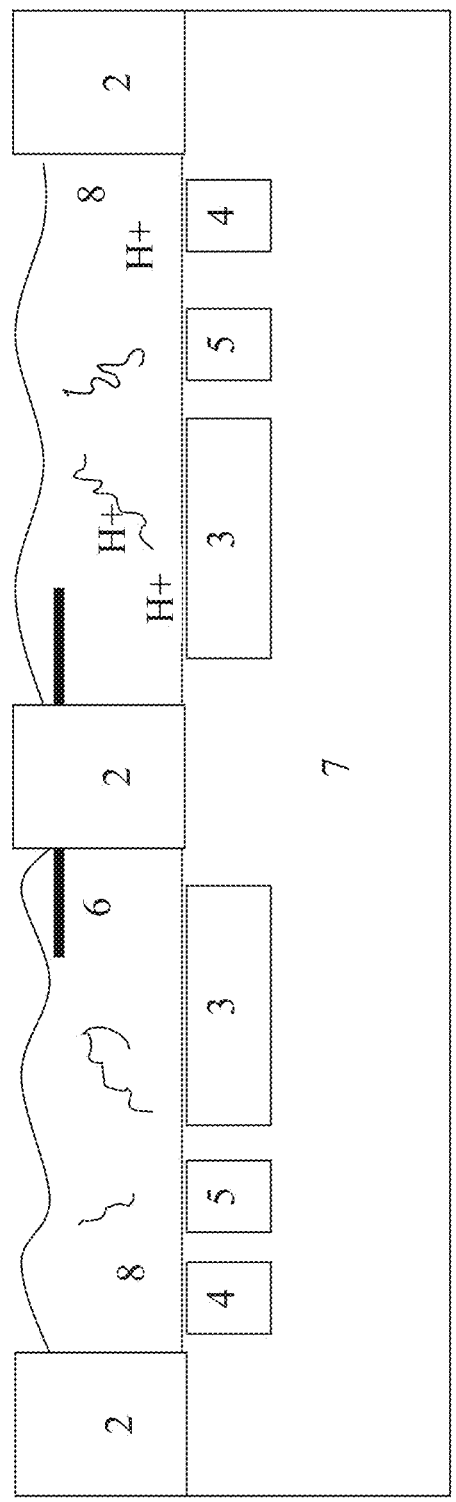
FIG. 3 is a profile view of a pH detection system.

Preferably, the pH sensor or indicator is an ISFET (Ion Sensitive Field Effect Transistor). This is shown in FIG. 3, wherein the pH sensor(s) 3 may be one or more Ion Sensitive Field Effect Transistors (ISFET) on a CMOS microchip 7, having thereupon microfluidic chambers 8 defined by voids in substrate 2. Reagents and nucleic acid sample may be combined before or after being added to one or more chamber(s) exposed to the ISFET(s). Each ISFET outputs an electrical signal which is monitored by a signal processor. The passivation layer of the ISFET can be functionalised to be sensitive to protons (hydrogen ions). As the nucleic acid amplifies, protons will be released and be detected by the signal processor as a change in the electrical output of the ISFET.

In an alternative embodiment, a pH indicator may be used to detect protons released during amplification. For example, the pH indicator may be a colorimetric or fluorescent dye, which changes optical properties such as emitted wavelength from the dye as the pH of the contacting fluid changes. Examples of pH indicators include Fluorescein, Pyranine, and pHrodo dye (available from Life Technology).

The microfluidic structure may be a well, chamber, or channel to receive the sample proximate the sensor or indicator and may comprise means for delivering the sample to the sensor or indicator. The microfluidic structure also helps reduce diffusion of protons away from the sensor or indicator. In the following embodiments, ISFETs are used to illustrate the pH detection scheme but other pH sensors could be used. The chamber may be defined by a cavity in a material such as SU-8, which is deposited on top of the microchip and selectively etched away to leave said cavities.

Figure 2:
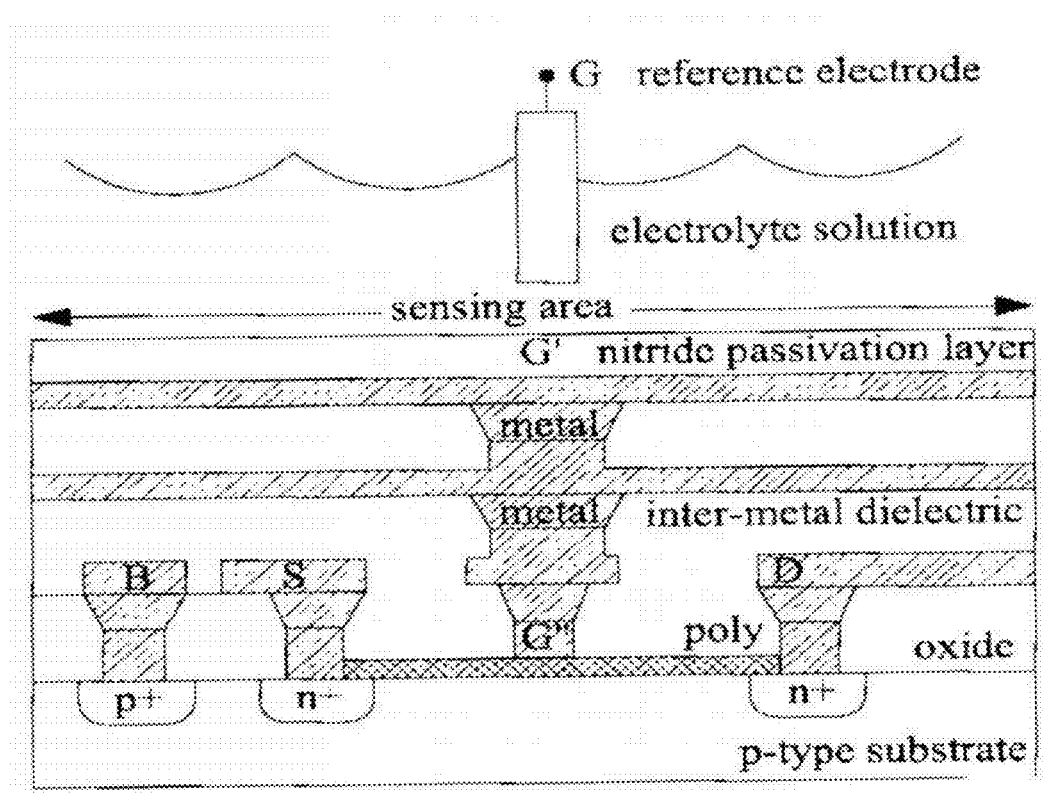
FIG. 2 is a profile view of an ISFET exposed to a sample.

FIG. 2 shows an ISFET with a floating gate and sensing layer made of Silicon Nitride which is exposed to the fluid electrolyte. ISFETS are further described in patent US2004134798 (A1), incorporated herein by reference.

Preferably each ISFET generates a normalised output signal from the difference between the ISFET and a reference signal. The reference signal may be derived from another ISFET exposed to a negative control reaction or a FET located on the chip but not exposed to fluctuating pH. Thus any common drift or noise on the chip will be cancelled by taking the difference between these signals.

The preferred amplification reaction is an isothermal amplification reaction, preferably a strand displacement reaction. As used herein, a strand displacement reaction is provided by a polymerase with strand displacement activity and reaction conditions where strand displacement is possible. Examples of strand displacement reactions include Strand displacement amplification (SDA), multiple displacement amplification (MDA), rolling circle amplification (RCA) or Loop mediated isothermal Amplification (LAMP).

Figure 1:
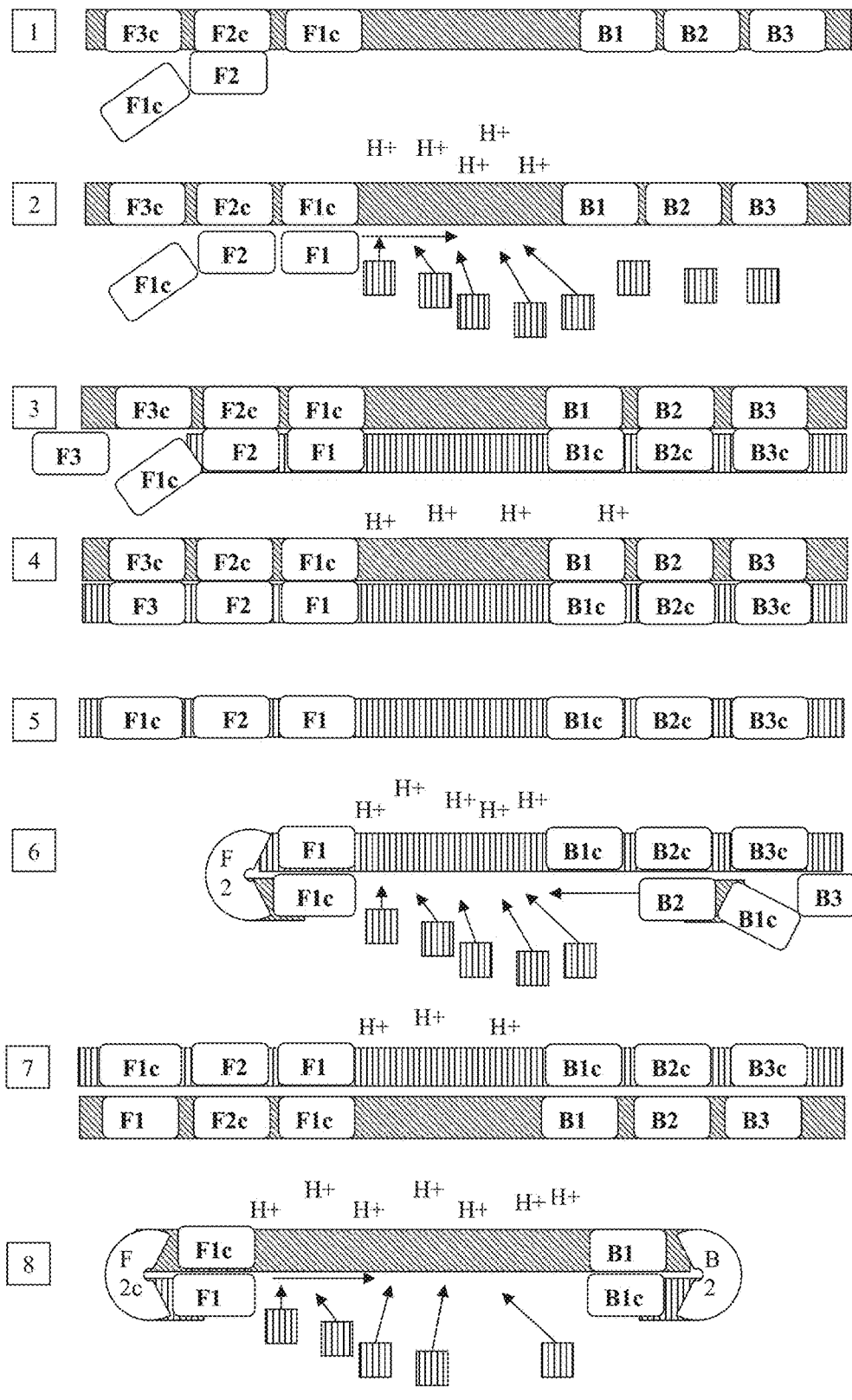
FIG. 1 is a series of chemical reactions is a strand displacement amplification technique such LAMP.

As an example, the steps in the chemical reaction of the LAMP method are illustrated in FIG. 1. In step 1, a double stranded DNA template at an elevated temperature is in dynamic equilibrium. Primers F2 can anneal to the single strand at the complementary position. In step 2 a polymerase with strand displacement activity enables nucleotides to extend along the template from the 3' end of F2. The incorporation of nucleotides is a reaction that has hydrogen ions (protons) as one of the by-products. In step 3, the F3 primer anneals to the F3c region on the template and begins displacement of the strands. The top strand is synthesized in step 4 releasing further protons. The bottom strand becomes a single strand (step 5) which forms a stem-loop as F1c anneals to F1 at the 5' end in step 6. At the same time the BIP primers, anneal to the other end of the strand and nucleotide extend from B2, releasing more protons. Primer B3 displaces the strands and promotes extension to create the double strand shown in step 7. The structure in step 8 has a double ended stem-loop from which continuous displacement and extension to amplify the template. As before the extension is associated with proton release.

The strand displacement polymerase used in the isothermal amplification reaction described herein may be chosen from the group: phi29-DNA-Polymerase, Klenow DNA-Polymerase, Vent DNA Polymerase, Deep Vent DNA Polymerase, Bst DNA Polymerase, 9oNm™ DNA Polymerase, and mutants and variants thereof.

The skilled person will appreciate that the optimal reagent concentrations will depend on the selection of the polymerase and that some modification to the preferred reagents below will be normal practice from knowledge of or experimentation with the polymerase. Guidance on appropriate conditions is available from the enzyme manufacturers.

Preferred Reagent Concentrations

The present method does not require any buffering agent and it is preferable that minimal buffering agent is present. A buffering agent is a weak acid and its conjugate base used to maintain the acidity (pH) of a solution near a chosen operating point such that the pH varies insignificantly when a small amount of strong acid or base is added, or in the present case, when a small amount of protons are released during the incorporation of nucleotides. A buffering agent is a compound added to a mixture having the primary purpose of providing buffering against changes in pH. As used herein, a compound whose primary purpose is other than buffering or whose buffering effect is much less than another compound in the mixture is not a buffering agent. Buffering agents for nucleic acid amplification reactions typically have a pKa value between 6 and 8.5, and has a buffering range between 6 and 9. For example, ammonium (NH4+) has some buffering capability but its main purpose is not to buffer the mixture and with a pKa of 9.24 operating in a mixture of pH 8, it is not a very strong buffer compared to Tris.

The choice of buffering agent, enzyme, and initial pH of the system are interdependent. For example, whilst the buffering agent may be one of the following common buffering agents TAPS, Bicine, Tris, Tricine, TAPSO, HEPES, TES, MOPS, PIPES, Cacodylate, SSC, and MES, in one embodiment TRIS is used with BST enzyme at a pH of 8.5.

Preferably the concentration of buffering agent is less than 10 mM, more preferably less than 8 mM, less than 5 mM, or less than 1 mM. Preferably the buffering agent is Tris or Hepes.

To reduce the effect of poisoning on the reference electrode, the concentration of sulphate compounds in the combined fluid is less than 15 mM, preferably less than 10 mM, less than 8 mM, less than 5 mM, or less than 1 mM.

Ammonium chloride can be used instead of ammonium sulphate whilst still allowing good amplification yield. More generally other quaternary salts can be substituted for ammonium chloride. Quaternary ammonium salts are positively charged polyatomic ions of the structure NR4+, where R is an alkyl or aryl group. Guanidine hydrochloride and ammonium chloride are examples of quaternary ammonium salts.

Preferably the range of concentration of quaternary ammonium salts in the combined fluid is greater than 2 mM, 5 mM, or 8 mM. However, ammonium (NH4+) has some buffering capability, thus the final concentration of ammonium compounds, such as ammonium chloride, in the combined fluid needs to be minimised whilst still maintaining optimal amplification yield. To reduce the buffering capacity, the concentration of ammonium compounds in the combined fluid is less than 15 mM, preferably less than 10 mM.

Magnesium is useful in promoting nucleotide incorporation in the template. The concentration of magnesium compounds, for example magnesium sulphate, in the combined fluid is preferably greater than 0.5 mM, greater than 1 mM, greater than 2 mM, or greater than 4 mM. The concentration of magnesium ion in the combined fluid is dependent on the concentration of dNTP, template and primers. In general, the preferred ratio of dNTP to magnesium sulphate in the combined fluid is less than 1:2, less than 1:3, less than 1:4 or less than 1:5.

Since high chloride concentration aids the Ag/AgCl electrode, monovalent salt such as sodium chloride or potassium chloride is added, the chloride ion concentration being preferably more than 10 mM, more than 20 mM, more than 30 mM, more than 40 mM or more than 50 mM. In one embodiment, the chloride ion concentration in the fluid is between 40 mM and 60 mM.

To set the starting pH of the fluid an alkali base, such as NaOH, LiOH or KOH, is added to the fluid. The concentration of the alkali base is designed to set the pH of the combined solution between 6 and 9, more preferably between 7 and 8.8, most preferably between 8 and 8.6, these pH ranges being desirable for certain enzymes to operate. For Bst polymerase, the preferred starting pH is more than 7, more preferably more than 8.2 and less than 8.8, more preferably less than 8.6.

The concentration of other reagents may be kept at normal amounts. See Notomi T et. al. Nucleic Acids Res. 2000 Jun. 15; 28(12): E63. For example in one embodiment, the amount of Bst polymerase is at least 0.3 Unit per microliter of combined fluid; the concentration of Betaine is 0-1.5M, preferably 0.8M-1M; and the total concentration of primers is between 2 m and 6.2 uM.

The above reagent concentrations have been found to provide good amplification yield and at the same time low buffering capacity such that a pH sensor can be used to detect protons released during amplification of the nucleic acid.

The process can take place at a fixed temperature, reducing the sensor signal drift associated with thermocycling, thus making the sensor signals more stable. Additionally the process is highly compatible with semiconductor platforms. For example, the optimal enzymatic temperature can be achieved and monitored with on-chip heating elements and temperature sensors; there is less concern over thermal expansion and thermal fatigue associated with thermocycling; and the reagents are chosen so as not to affect the electrodes on the microchip.

Typically, isothermal methods require a set temperature, which is determined by the reagents being used. For example, in LAMP the enzymes function best between 60 and 65° C. Advantageously the reagents/buffer of preferred embodiments described herein enables a wider operating temperature.

Because isothermal amplification, unlike thermocycling, does not involve discrete steps, each step doubling the DNA, it is difficult to estimate how much amplification has taken place at a given time. As a result, such isothermal amplification methods normally encourage excess amplification with the side effect that the background (i.e. non-specific) amplification or fluorescent background level is very high. The present method enables real time detection of the amplification process such that the process can be stopped when sufficient yield has been obtained. In the case where the present method takes place on a microchip, the fluid being monitored by a pH sensor and heated by elements in the chip surface, the temperature can be dropped or raised to a point where amplification becomes suspended. This ensures that there is sufficient desired DNA beyond the background DNA without waiting unnecessarily to be sure that sufficient amplification has occurred.

The reagents are provided in the concentrations above when combined. Some reagents may be stored separately prior to mixing having their own required conditions for stability. For example, the enzyme may be stored long term in a moderately buffered solution separate from the other reagents to ensure stability of the enzyme. Upon mixing with the remaining reagents, the buffering agent becomes sufficiently diluted so as not to significantly mask a pH change. In addition, primers for specific genes of interest may be provided in a separate solution or in a lyophilized form. The conditions and pre-mix concentrations will be known to or derivable by the skilled person in consideration of the reagent to be used.

Applications

Figure 4:
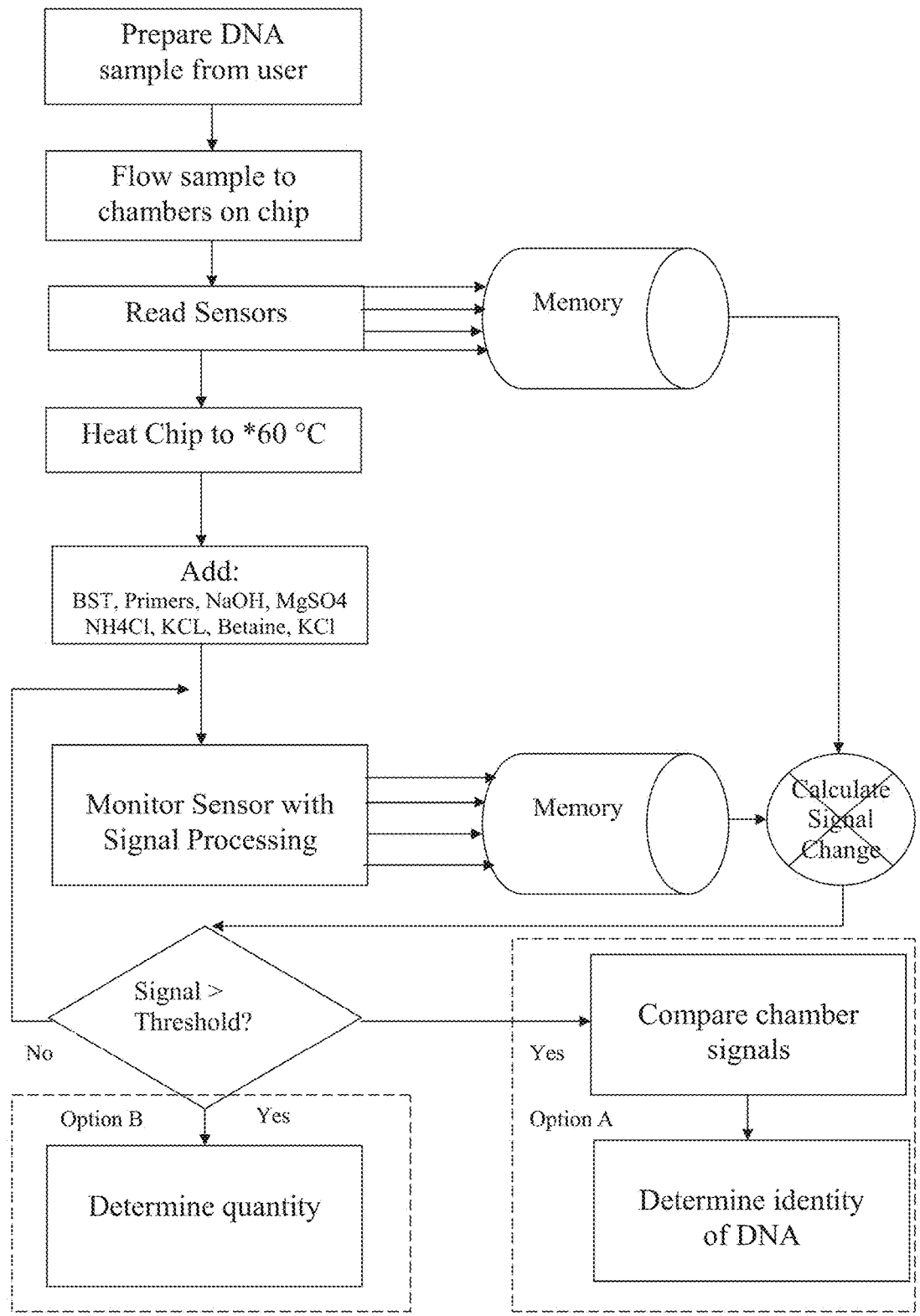
FIG. 4 is a flowchart of a method to monitor amplification of a DNA sample for (option A) identifying the DNA or (option B) calculating the quantity of DNA.
Figure 5:
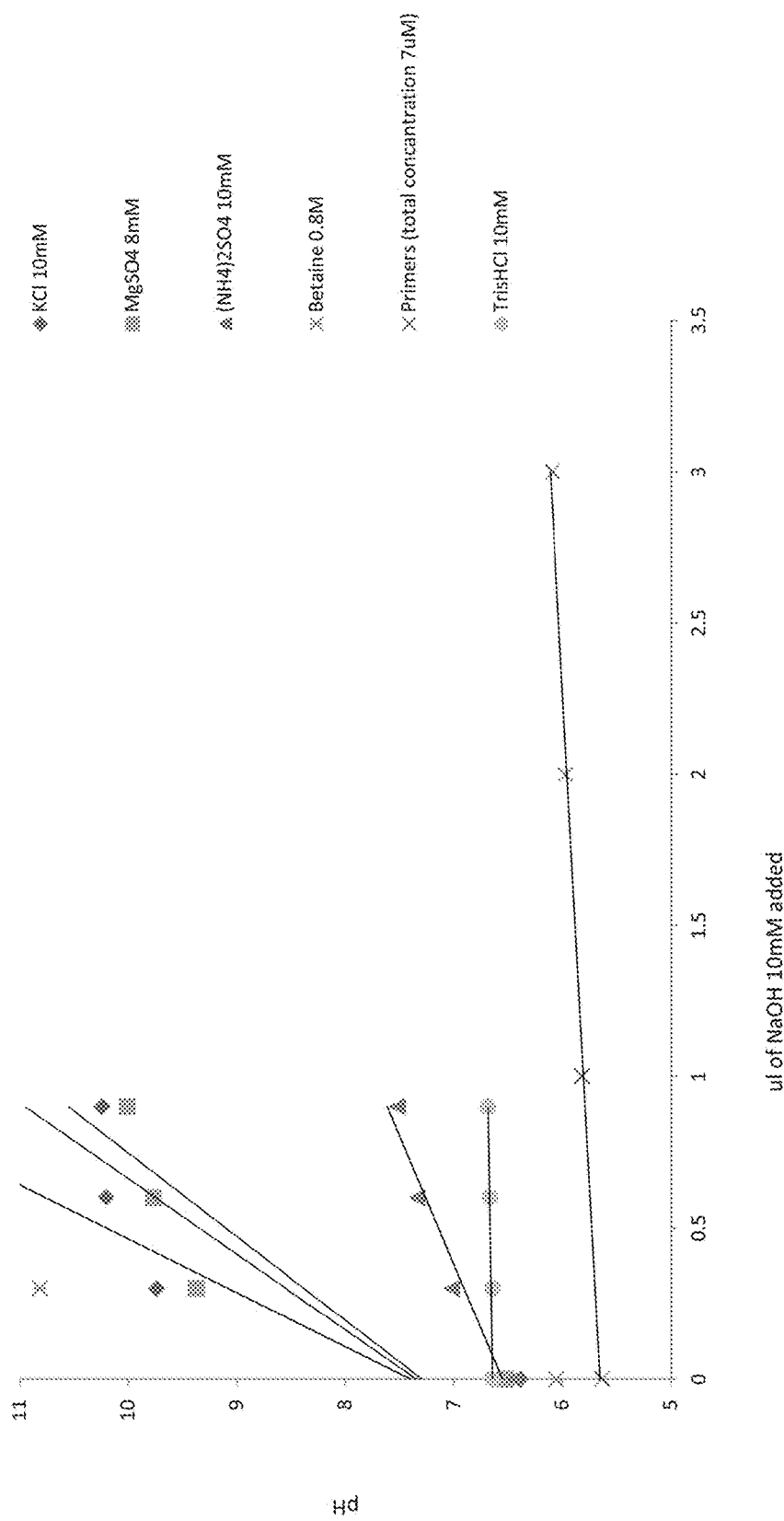
FIG. 5 is a chart of buffering capacity of reagents in a normal LAMP recipe.
Figure 6:
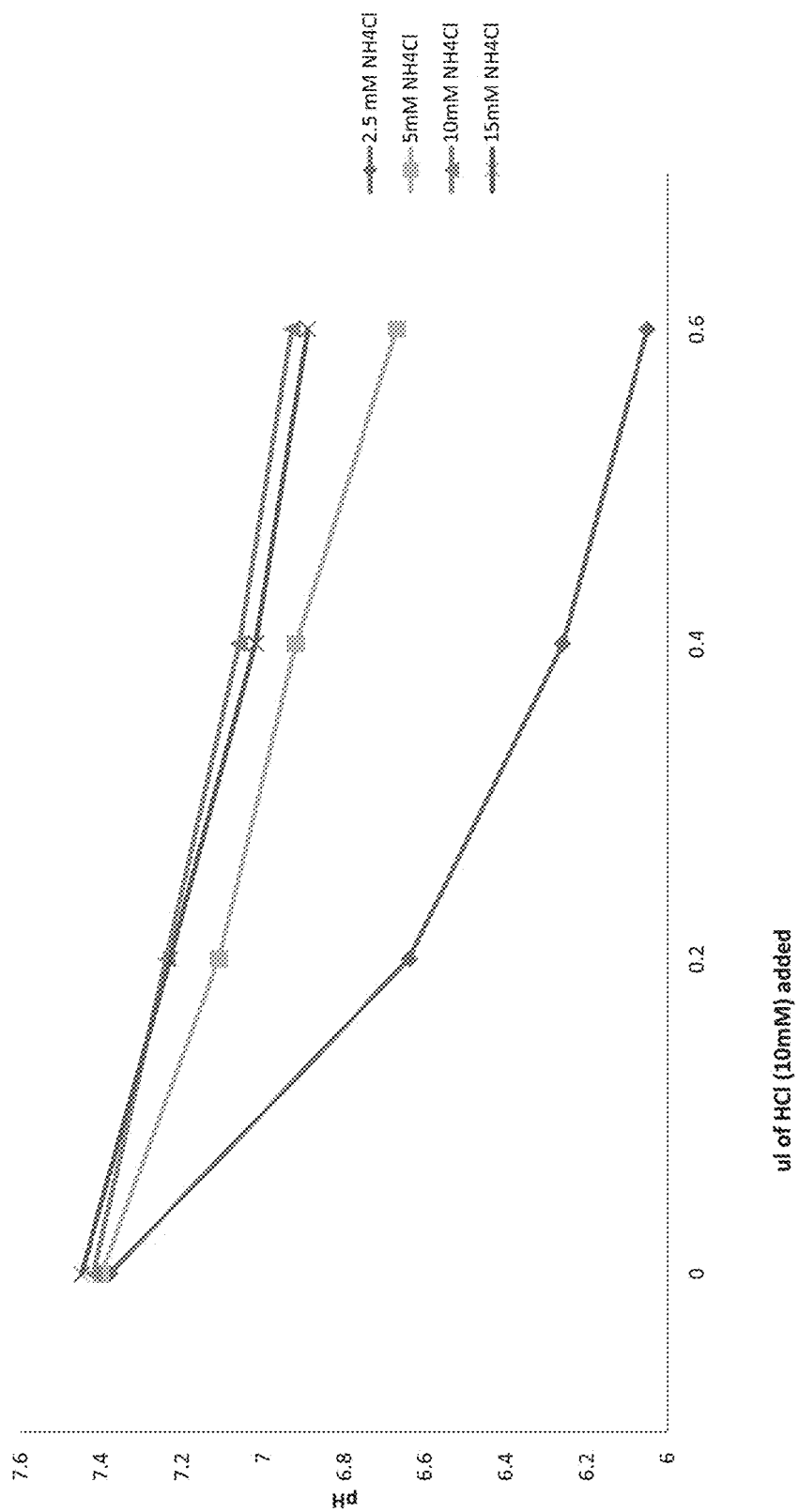
FIG. 6 is chart showing the buffer capacity of different concentrations of NH4Cl.

As illustrated by the flowchart of FIG. 4, a DNA sample may be prepared and divided into one or more chambers or wells. Each chamber or well is exposed to an ISFET on a microchip. The DNA is combined with reagents for loop-mediated isothermal amplification. The following are individually preferred reagents and concentrations, wherein the combination is the most preferred kit of reagents:

Bst polymerase of at least 0.3 Unit per microliter;
a concentration of Betaine of 1M;
a total concentration of primers of 5 uM;
a concentration of Magnesium Sulphate of 5 mM;
a concentration of Tris of 1 mM;
a concentration of Ammonium Sulphate of zero;
a concentration of NaOH of 1.2 mM which sets the pH of the combined fluid to 8.5 pH;
a concentration of Ammonium Chloride of 5 mM; and
a concentration of Potassium Chloride of 50 mM.

The ISFET signals are taken differentially with respect to a reference FET and are monitored by a signal processor. The chamber and fluid is heated to 60° C. by heaters integrated with the microchip. After a predetermined reaction period, sufficient template amplification, if possible, should have occurred to be detected as a change in the ISFET signal. The signal can also be continuously monitored to determine when the amplification and thus signal change has crossed a threshold amount.

Diagnostics

The method may be used to identify one or more bases in a nucleic acid strand as illustrated, in a preferred embodiment, by option A of FIG. 4. The identification may be a single base or a unique sequence. In the case where a unique sequence is identified, it is possible to identify certain bases that are associated with medical conditions and this knowledge of the bases can provide a method for diagnosis. Examples of bases of interest include unique sequences, Single Nucleotide Polymorphism (SNP), deletions, insertions, Short Tandem Repeats (STP) and mutations that may be inherited or somatically derived. Pathogen detection is also possible whereby the method may detect the presence of an organism or strain of organism.

Primers used in the amplification such as the FIP (forward inner primer) and BIP (back inner primer) oligos can be designed to include or exclude the sequence, SNP, or STP region. In this way the amplification or lack thereof indicates the presence or absence of the base(s)/sequence to be identified.

In the system shown in FIG. 1, two or more chambers or wells may be used to perform concurrent amplification of the DNA. Each well has added to it a different set of primers, each set of primers being adapted to detect a different base in the sample DNA. The DNA will therefore only amplify in the presence of the complementary set of primers, producing protons, whilst the others will not. Where only one chamber experiences amplification, the DNA will be considered homozygous, i.e. having identical alleles (mutant or wildtype) on both genes. Where two chambers experience amplification, the DNA will be considered heterozygous, i.e. having different alleles (mutant and wildtype) on the genes. One can thus determine the identity of the base(s) in the sample DNA by monitoring the ISFETs signals to detect a fluctuation combined with knowledge of the primer set in the corresponding well. To reduce signal processing requirements, the signals from ISFETs can be compared in real-time to output a signal representing the difference between amplification by-products in each well.

Quantification

The method may be used to quantify the amount of DNA in a sample as illustrated in FIG. 4, option B. The proton concentration at a given time will be proportional to the quantity of DNA in the fluid and the cumulative quantity of previous protons generated and which have not diffused away from the sensing area. By knowing the signal change from the start of the reaction at a given time and comparing this to a standard, one can determine the quantity of DNA in the sample at the start of the amplification. Thus one works backwards from the current quantity and time to determine the quantity of starting DNA in the sample.

Figure 7:
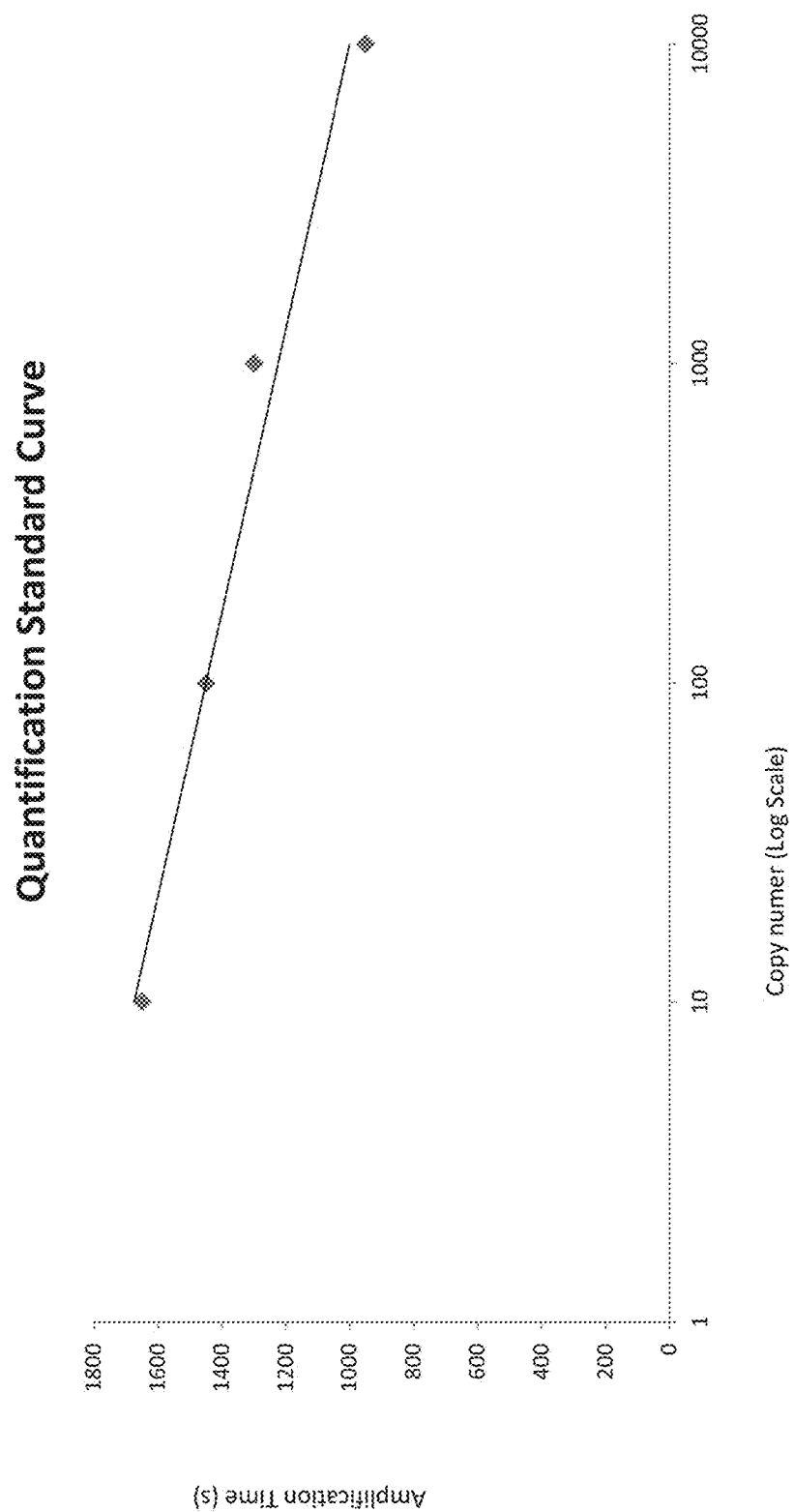
FIG. 7 is a chart of a standard curve for quantification of DNA in a sample.

The standard may be derived from a model, experimental data, or one or more separate internal control reactions undergoing an amplification reaction in parallel with the assay. The standard may be represented as a look-up-table on a storage medium or as a quantification equation in a computer program. FIG. 7 shows an exemplary graph of DNA quantity versus time to detect that quantity. The graph can be interpolated or extrapolated or can be used to extract a best-fit equation through the data to estimate DNA quantities once a reaction time has been measured.

The reaction time is the period from when amplification begins (i.e. when all reagents and conditions for amplification are present) to when the pH change becomes greater than a threshold. The pH change may be detected by monitoring the pH sensor signal or pH indicator.

RNA

The present method may also be used to detect RNA template through the use of a reverse transcriptase (RTase) enzyme such as avian myeloblastosis virus (AMV RTase) together with DNA polymerase. cDNA can be synthesized from template RNA and amplified with the present technique and then detected using an pH sensor or indicator.

Buffer Capacity Optimisation

Whilst most compounds contribute some buffering capacity to the mixture, the total contribution is ideally minimised. However some minimal buffer may be required to stabilise the enzymes. Selection of the buffer agent (if present at all), total reagent buffer capacity, and concentrations should be made in consideration of the expected protons generated by the amplification reaction. The amount of protons generated will depend on the amount of starting template, amplification conditions and amplification time (assuming excess nucleotides, enzyme and primers). The starting template will depend on the donor, type of biological sample taken and the amplification time may be chosen by the operator or manufacturer of the test. However from a knowledge of the amplification time, biological sample type, and donor type, one can calculate an expected amount (or range of amount) of protons to be generated.

The buffer capacity of the mixture can then be chosen such that a pH change greater than a threshold amount will result from the expected (or lowest expected) proton generation due to amplification even in the presence of the buffered mixture. The pH change threshold may be the limit of detection of the sensor and associated circuitry. Alternatively, the pH change threshold may be 0.1 pH, more preferably 0.2 pH, most preferably 0.5 pH.

Buffer capacity is defined by equation (I):

$$\beta = dn/d(p[H^+])$$

wherein n is an amount of added OH− or H+, and d(p[H$^+$]) is the resulting infinitesimal change in the cologarithm of the hydrogen ion concentration.

In an exemplary embodiment employing an ISFET having a lower detection limit of 0.5 pH, exposed to a 35 ul amplification reaction, wherein after 30 minutes the experimental yield is 50 ug of amplicons. The total protons released from the amplicon yield will be approximately 2.17 mM (assuming the molecular weight of a base pair is 650 g/mole);

$$\beta = 2.17 \text{ mM}/>0.5$$

$$\beta < 4.34 \text{ mM}$$

thus the buffer capacity of the mixture should be set to less than 4.34 mM in order to achieve a desired pH change of >0.5.

Table 1 below provides properties of common buffering agents with pKas at 25 C between 6.15 and 8.43. The concentration of these buffering agents should be minimized in the reaction to achieve greater pH change in a shorter amplification reaction time. However, the buffering agents may be optionally provided to reduce background noise, stabilize the enzyme and/or stabilize the initial reaction. Table 2 provides a calculation of the effect of the buffer capacity of amplification reactions suitable for Bst enzyme by varying the concentrations of buffer agents. As can be seen, a number of buffer options will satisfy the requirement above, having a buffer capacity of less than 4.34 mM (4340 uM). Each buffer agent and concentration listed in table 2 satisfying this condition are individually preferable and considered within the scope of this invention.

TABLE 1

Properties of various Buffer Agents

| Buffer Name | pKa at 25° C. | Buffer Range | Full Compound Name |
|---|---|---|---|
| TAPS | 8.43 | 7.7-9.1 | 3-{[tris(hydroxymethyl)methyl]amino}propanesulfonic acid |
| Bicine | 8.05 | 7.6-9.0 | N,N-bis(2-hydroxyethyl)glycine |
| Tris | 8.06 | 7.5-9.0 | tris(hydroxymethyl)methylamine |
| Tricine | 8.05 | 7.4-8.8 | N-tris(hydromethyl)methylglycine |
| TAPSO | 7.635 | 7.0-8.2 | 3-[N-Tris(hydroxymethyl)methylamino]-2-hydroxypropanesulfonic Acid |
| HEPES | 7.48 | 6.8-8.2 | 4-2-hydroxyethyl-1-piperazineethanesulfonic acid |
| TES | 7.4 | 6.8-8.2 | 2-{[tris(hydroxymethyl)methyl]amino}ethanesulfonic acid |
| MOPS | 7.2 | 6.5-7.9 | 3-(N-morpholino)propanesulfonic acid |
| PIPES | 6.76 | 6.1-7.5 | piperazine-N,N'-bis(2-ethanesulfonic acid) |
| Cacodylate | 6.27 | 5.0-7.4 | dimethylarsinic acid |
| SSC | 7 | 6.5-7.5 | saline sodium citrate |
| MES | 6.15 | 5.5-6.7 | 2-(N-morpholino)ethanesulfonic acid |

TABLE 2

Buffer capacity at various conditions

| Hepes @pH | | | | | |
|---|---|---|---|---|---|
| | 9 | 8.5 | 8 | 7.5 | 7 |
| 40 mM | | 8865 | 17121 | 23580 | 18235 |
| 20 mM | | 5199 | 8916 | 12071 | 9628 |
| 10 mM | 3352 | 3367 | 4813 | 6317 | 5324 |
| 5 mM | 3024 | 2451 | 2762 | 3440 | 3173 |

| Tris @pH | | | | | |
|---|---|---|---|---|---|
| | 9 | 8.5 | 8 | 7.5 | 7 |
| 40 mM | | 19536.4 | 23631 | 16160 | 7809 |
| 20 mM | | 10535 | 12170 | 8361 | 4415 |
| 10 mM | 4824 | 6035 | 6441 | 4462 | 2718 |
| 5 mM | 3761 | 3785 | 3575 | 2512 | 1869 |

| MOPS @pH | | | | | | |
|---|---|---|---|---|---|---|
| | 9 | 8.5 | 8 | 7.5 | 7 | 6.5 |
| 40 mM | | 5721 | 11589 | 21050 | 22871 | 14673 |
| 20 mM | | 3628 | 6149 | 10806 | 11946 | 8286 |
| 10 mM | 3051 | 2581 | 3430 | 5685 | 6483 | 5092 |
| 5 mM | 2874 | 2058 | 2070 | 3124 | 3752 | 3496 |

| Bicine @pH | | | | | | |
|---|---|---|---|---|---|---|
| | 9 | 8.5 | 8 | 7.5 | 7 | 6.5 |
| 40 mM | | 23891 | 20371 | 10553 | 4791.26 | 3164 |
| 20 mM | | 12713 | 10541 | 5558 | 2906 | 2531 |
| 10 mM | 6139 | 7124 | 5626 | 3061 | 1963 | 2215 |
| 5 mM | 4418 | 4329 | 3168 | 1812 | 1492 | 2057 |

In some embodiments, the buffer capacity is reduced from the calculated maximum by a factor to ensure that sufficient pH signal is detected. The buffer capacity may be less than one-half, preferably less than one-fifth, or less than one-tenth the maximum buffer capacity for which a pH change due to an expected proton release from an amplification reaction is detectable. Thus in the example above the buffer capacity may be set to 1/10 of 4.34 mM, i.e. 0.434 mM.

In one embodiment, the buffer capacity of the reagents in the fluid is arranged to mask a pH change that would otherwise result even in the absence of successful amplification of the target nucleic acid. This change can be considered ionic background noise, which may result from non-specific amplification or spontaneous degradation and hydrolysis of nucleotides, primers, or template. Non-specific amplification refers to nucleic acid amplification products that are not derived from the targeted region of the template nucleic acid. Typically this results from primer-dimer formation and/or primers annealing to non-targeted regions of the template DNA.

In one embodiment, the total buffer capacity of the mixture is set such that background noise can be ignored. For example, the amount of background noise that may be produced during the method can be estimated or found from experiment and expressed as a change in pH. The buffer capacity of the reagents can be increased, beyond the minimal amount suggested above for providing a low limit of detection, to an amount that masks the background by absorbing the protons released or consumed due to the background. Therefore no signal is detected by the pH sensor or indicator unless and until there is sufficient proton release which should thus correspond to specific nucleotide insertion for the target template nucleic acid.

In one embodiment, a DNA sample and reagents are added to multiple microfluidic chambers. In an exemplary embodiment, the pH drop due to background in the absence of a buffer is estimated at 0.1 pH. A small amount of buffer is provided to each chamber to mask this estimated effect. The sensor signal is monitored before, during, and after the chemical reactions take place. Only in the chamber(s) where there is a nucleic acid amplification reaction releasing significant protons will there be a detectable change in the sensor signal. Thus in one embodiment the buffer capacity is greater than 0.5 mM.

Different reagents, such as allele specific primers, may be used to detect the presence or absence of genetic biomarkers on the sample. The reaction may be amplification of DNA and the reagents may comprise primers and nucleotides suitable for thermocycling or isothermal amplification. As amplification of target DNA proceeds in one or more chambers, protons are released beyond the estimated background effect masked by the buffer. The pH change is detected as a change in the sensor signal.

The invention claimed is:

1. An apparatus for monitoring isothermal amplification of a nucleic acid comprising:
    a pH sensor or pH indicator;
    a nucleic acid in an amplification mixture comprising a magnesium salt, an alkali base, and at least one of: a quaternary ammonium salt, ammonium chloride, or guanidine hydrochloride, wherein the mixture has a buffer capacity less than 10mM and is in communication with the pH sensor or pH indicator; and
    an isothermal amplification enzyme.

2. The apparatus of claim 1, wherein the pH indicator is a colorimetric or fluorescent dye.

3. The apparatus of claim 1, wherein the pH sensor is an Ion Sensitive Field Effect Transistor (ISFET).

4. The apparatus of claim 1, further comprising a reference electrode in fluid communication with the amplification mixture.

5. The apparatus of claim 1, wherein the mixture further comprises one or more allele specific primers having at least one base complementary to a target Single Nucleotide Polymorphism (SNP) of the nucleic acid.

6. The apparatus of claim 1, wherein the buffer capacity of the mixture is set to less than 5 mM.

7. The apparatus of claim 1, wherein the buffer capacity of the mixture is set to less than 1 mM.

8. The apparatus of claim 1, wherein the mixture further comprises a buffering agent.

9. The apparatus of claim 8, wherein the buffering agent is selected from the group consisting of Tris, HEPES, bicine, and MOPS.

10. The apparatus of claim 9, wherein the concentration of the buffering agent in the mixture is less than 5 mM.

11. The apparatus of claim 1, wherein the mixture further comprises sulphate compounds.

12. The apparatus of claim 11, wherein the concentration of the sulphate compounds in the mixture is less than 15 mM.

13. The apparatus of claim 1, wherein the concentration of the quaternary ammonium salt, ammonium chloride, or guanidine hydrochloride in the mixture is between 2 mM and 15 mM.

14. The apparatus of claim 1, wherein the concentration of the alkali base sets the pH of the mixture between 6 and 9.

15. The apparatus of claim 1, wherein the alkali base is one of NaOH, KOH, or LiOH.

16. The apparatus of claim 1, wherein the mixture further comprises one or more primers used in the amplification of the nucleic acid, which primers are allele specific such that amplification indicates the presence of a target nucleic acid.

17. The apparatus of claim 1, wherein the isothermal amplification enzyme is a Strand Displacement polymerase.

18. The apparatus of claim 1, wherein the isothermal amplification enzyme is a Loop-mediated isothermal amplification (LAMP) enzyme.

19. The apparatus of claim 1 further comprising a microfluidic structure configured to receive the amplification mixture.

20. The apparatus of claim 19, wherein the microfluidic structure is exposed to the pH sensor.

* * * * *